US008546771B2

(12) United States Patent
Kraemer et al.

(10) Patent No.: US 8,546,771 B2
(45) Date of Patent: Oct. 1, 2013

(54) METHOD AND DEVICE FOR IDENTIFYING A PHOTOLUMINESCENT MATERIAL

(75) Inventors: Udo Kraemer, Vilshofen an der Donau (DE); Walter Braumandl, Thurmansbang (DE)

(73) Assignee: Sensor Instruments Entwicklungs-und Vertriebs GmbH, Thurmansbang (DE)

( * ) Notice: Subject to any disclaimer, the term of this patent is extended or adjusted under 35 U.S.C. 154(b) by 0 days.

(21) Appl. No.: 13/552,248

(22) Filed: Jul. 18, 2012

(65) Prior Publication Data
US 2013/0020504 A1   Jan. 24, 2013

(30) Foreign Application Priority Data

Jul. 20, 2011   (DE) .......................... 10 2011 108 180

(51) Int. Cl.
*G01N 21/64* (2006.01)
(52) U.S. Cl.
USPC ...................................................... 250/459.1
(58) Field of Classification Search
USPC ...................................................... 250/459.1
See application file for complete search history.

(56) References Cited

U.S. PATENT DOCUMENTS

| 5,381,016 | A  | 1/1995  | Moriya          |
| 6,252,660 | B1 | 6/2001  | Frisch et al.   |
| 6,448,018 | B1 | 9/2002  | Nakayama et al. |
| 6,459,093 | B1 | 10/2002 | Dieckmann       |
| 2005/0224040 | A1 | 10/2005 | Kusumi et al. |
| 2007/0139639 | A1 | 6/2007  | Tsien et al.  |
| 2008/0003610 | A1 | 1/2008  | Frank et al.  |
| 2008/0048128 | A1 | 2/2008  | Braumandl     |
| 2009/0148350 | A1 | 6/2009  | Pham et al.   |
| 2009/0261269 | A1* | 10/2009 | Horii et al. ................. 250/459.1 |
| 2011/0293154 | A1* | 12/2011 | Meixner et al. ............... 382/128 |

FOREIGN PATENT DOCUMENTS

| CH | 609 777 | 3/1979 |
| DE | 693 15 877 T2 | 4/1998 |
| DE | 699 12 361 T2 | 8/2004 |
| DE | 10 2004 016 249 A | 10/2005 |
| DE | 10 2004 039 035 A | 10/2005 |
| DE | 699 26 983 T2 | 6/2006 |

(Continued)

OTHER PUBLICATIONS

Office Action dated Sep. 16, 2011 from German Patent & Trademark Office for priority DE application No. 10 2011 106 180.5 (with translation of substantive portions thereof).

*Primary Examiner* — Kiho Kim
(74) *Attorney, Agent, or Firm* — J-TEK Law PLLC; Jeffrey D. Tekanic

(57) ABSTRACT

A method for identifying a photoluminescent material that, after excitation with excitation light, emits emission light having different wavelengths is disclosed. The method includes irradiating the photoluminescent material with the excitation light, detecting a temporal intensity curve of at least two emission light components having different wavelengths, which components are emitted from the photoluminescent material as a result of the excitation, calculating initial intensities of the emission light components at a common time, determining at least one intensity parameter by correlating the calculated initial intensities, determining at least one decay parameter value for each of the emission light components from a time progression of their intensity and identifying the photoluminescent material using the intensity parameter(s) and the decay parameter values. A device configured to identify the photoluminescent material includes an excitation light source, a receiving apparatus, an evaluation apparatus and a control apparatus that performs the photoluminescent material identifying method.

20 Claims, 3 Drawing Sheets

(56) References Cited

FOREIGN PATENT DOCUMENTS

| DE | 10 2005 006 237 A | 8/2006 |
| DE | 698 38 090 T2 | 3/2008 |
| DE | 699 37 126 T2 | 6/2008 |
| DE | 10 2009 010 446 A | 9/2010 |
| DE | 10 2009 038 356 A | 3/2011 |
| EP | 1 158 459 A1 | 11/2001 |

* cited by examiner

METHOD AND DEVICE FOR IDENTIFYING A PHOTOLUMINESCENT MATERIAL

CROSS-REFERENCE

This application claims priority to German patent application no. 10 2011 108 180.5, filed on Jul. 20, 2011, the contents of which are incorporated by reference as if fully set forth herein.

TECHNICAL FIELD

The present invention generally relates to methods and devices for identifying a photoluminescent material.

BACKGROUND

Luminescent materials are increasingly being used to authenticate a variety of objects. Luminescent materials convert energy from excitation light of a predetermined wavelength into emission light of one or more different wavelengths. Most luminescent materials can be excited with excitation light that comprises different wavelengths. Some luminescent materials emit emission light having two or more different wavelengths even if they are excited with excitation light of only one wavelength.

If the emitted radiation has a longer wavelength than the excitation radiation, it is called "Stokes" or "down-converting" luminescence. On the other hand, if the emitted light has a shorter wavelength than the excitation light, it is called "anti-Stokes" or "up-converting" luminescence.

There are two different types of luminescence: fluorescence and phosphorescence. Fluorescence is the instantaneous emission of emission light upon irradiating a fluorescent material with excitation light. In phosphorescent materials, on the other hand, the emission is delayed relative to the excitation, so that phosphorescent materials phosphoresce or glow after the excitation light has been turned off. The phosphorescence duration and the decay of the phosphorescence are material-specific.

A method for authenticating a marking, i.e. for determining whether a marking comprises a specific photoluminescent material, is known from EP 1 158 459 A1, which discloses the following steps:
- exciting the marking with at least one excitation light pulse,
- after the excitation, measuring intensity values of the emission light at predetermined time intervals,
- forming a function representing the intensity as a function of time, and
- comparing the function with at least one reference function, wherein the function and the reference function are normalized prior to the comparison.

SUMMARY

It is an object of the present teachings to provide a method and/or a device for the identification of a photoluminescent material, which preferably provide(s) a more reliable identification of the photoluminescent material.

In one aspect of the present teachings, a method for identifying a photoluminescent material, which emits emission light having different wavelengths after excitation with excitation light, is disclosed. The method may include the following steps:
- Exciting the photoluminescent material with excitation light,
- Detecting the temporal intensity curve of at least two emission light components having different wavelengths (or different ranges of wavelengths), which components are emitted from the photoluminescent material as a result of the excitation,
- Determining initial intensities of the respective emission light components at a common time,
- Determining an intensity parameter by correlating the determined initial intensities,
- Determining at least one decay parameter value for each of the emission light components from the time progression of their intensity and
- Identifying the photoluminescent material using the intensity parameter and the decay parameters.

According to this aspect of the present teachings, two different wavelengths or wavelength ranges of the emission light are synchronously or simultaneously evaluated. The relative initial intensities of the emission light components of the different wavelengths or wavelength ranges and their respective decays provide a kind of "fingerprint" for the photoluminescent material, which can be advantageously utilized to reliably identify the particular photoluminescent material.

The photoluminescent material may be excited with at least one excitation light pulse of a predetermined wavelength and the initial intensities of the emission light components may be immediately or promptly determined/calculated after the termination of the excitation light pulse. In this respect, the term "immediately" is preferably understood as meaning within 100 μs, more preferably within 10 μs, of the switching off (termination) of the excitation light.

In addition or in the alternative, the photoluminescent material may preferably be an up-converting (Stokes) material. In such an embodiment, the wavelength(s) of the excitation light is longer than the wavelengths of the detected emission light components.

In addition or in the alternative, a predetermined intensity function may include at least one initial intensity parameter and at least one decay parameter. The predetermined intensity function may be brought into optimal agreement with the determined intensity curve of the respective emission light component.

For example, this intensity function may be generally represented as follows:

$$y_i = \sum_{j=0}^{m} A_j e^{-(\tau_j \times i \times \Delta t)} + A_0,$$

wherein:
$y_i$ = the intensity of an emission light component at time $i \times \Delta t$, wherein i is the number of samples and $\Delta t$ is the sampling interval (the inverse of the sampling rate), such that $i \times \Delta t$ represents the amount of time that has elapsed since the maximum (initial) intensity was achieved, $A_j$ = the initial intensity of one part (e.g., one wavelength or a range of wavelengths) of the emission light component, $\tau_j$ = the decay parameter of the one (same) part (e.g., one wavelength or a range of wavelengths) of the emission light component, j = the number of parts (e.g., one wavelength or a range of wavelengths) in the emission light component and $A_0$ = a constant ambient (background) light component.

As a further example, this intensity function may be represented more simply for a single emission light component (one wavelength or one range of wavelengths) as follows:

$$y_i = A e^{-(\tau \times i \times \Delta t)} + A_0,$$

wherein:

$y_i$=the intensity of the emission light component (wavelength or range of wavelength) at time $i \times \Delta t$, wherein i equals the number of samples and $\Delta t$ equals the sampling interval (the inverse of the sampling rate), such that $i \times \Delta t$ represents the amount of time that has elapsed since the maximum (initial) intensity was achieved, A=the initial (maximum) intensity of the emission component (wavelength or range of wavelength), τ=the decay parameter of the emission light component (wavelength or range of wavelength), and $A_0$=a constant ambient (background) light component.

In addition or in the alternative, the method may further include the following additional steps:

Storing previously-determined intensity parameters and decay parameter values for a plurality of predetermined photoluminescent materials and Identifying the photoluminescent material by comparing the intensity parameter(s) and decay parameter(s), which have been calculated/determined for the to-be-identified material, with the corresponding stored values.

In another aspect of the present teachings, a device is disclosed for identifying a photoluminescent material that, after excitation with excitation light, emits emission light having at least two different wavelengths. The device may include:

an excitation light source configured to illuminate/irradiate the photoluminescent material, a receiving apparatus configured to detect the emission light radiated/emitted from the photoluminescent material as a result of its excitation with the excitation light, the receiving apparatus including at least two receiver units configured to respectively detect emission light components having different wavelengths, an evaluation apparatus configured to evaluate the emission light components detected by the receiver units with regard to their intensities and their time progression and a control apparatus configured to control of the operation of the excitation light source and the evaluation apparatus in accordance with any of the above- or below-described methods.

The device may further include:

a storage device configured to store intensity parameters and decay parameters of a plurality of predetermined photoluminescent materials according to the above-described method step and a comparison device configured to perform the comparison according to the above-described method step.

In addition or in the alternative, the receiver units may comprise optical filters having different wavelength-dependent transparencies.

In addition or in the alternative, the device may further comprise a sensor head and optical light guides that end at the sensor head. The light guides are connected with the excitation light source and the receiver units.

Furthermore, the end surfaces of the light guides, which are connected with the excitation light source and the receiver units, may each be disposed in a distributed manner in single sensor surface of the sensor head at least substantially over its end surface.

The present teachings may be advantageously utilized to authenticate any markings containing one or more photoluminescent materials that, after excitation with excitation light of one or more predetermined wavelengths, emit(s) emission light having at least two different wavelengths. More particularly, the present teachings are especially well suited for identifying up-converting (Stokes) photoluminescent materials.

Further objects, advantages, features, embodiments and details of the invention will be readily understood by the skilled person upon reading the following detailed description and claims in view of the appended drawings.

DETAILED DESCRIPTION OF THE INVENTION

Representative, non-limiting examples or exemplary embodiments of the present invention will be described below in greater detail. This detailed description is merely intended to teach a person of skill in the art further details for practicing preferred aspects of the present teachings and is not intended to limit the scope of the invention. Furthermore, each of the additional features and teachings disclosed above may be utilized separately or in conjunction with other features and teachings to provide improved methods and devices for identifying a photoluminescent material.

Moreover, combinations of features and steps disclosed in the following detailed description may not be necessary to practice the invention in the broadest sense, and are instead taught merely to particularly describe representative examples of the invention. Furthermore, various features of the above-described aspects, features and representative examples, as well as the various independent and dependent claims below, may be combined in ways that are not specifically and explicitly enumerated in order to provide additional useful embodiments of the present teachings.

All features disclosed in the description and/or the claims are intended to be disclosed separately and independently from each other for the purpose of original written disclosure, as well as for the purpose of restricting the claimed subject matter, independent of the particular combination of features in the embodiments and/or the claims. In addition, all value ranges or indications of groups of entities are intended to disclose every possible intermediate value or intermediate entity for the purpose of original written disclosure, as well as for the purpose of restricting the claimed subject matter.

It is expressly noted that all of the above- or below-described (or claimed) functions may be implemented in any of the following exemplary embodiments, e.g., by appropriately programming the controller(s) of the device, which may be embodied with one or more processors (e.g., microprocessors) and memory/storage that stores programs and data to be executed by the processor(s). In the alternative, some or all of the above- or below-described functions may be implemented in analog circuitry, dedicated digital circuitry, e.g., a state machine, or mixed dedicated circuitry in any of the below-described exemplary embodiments, as would be well understood by a person of ordinary skill in the art after reading the present disclosure.

Figure 1:
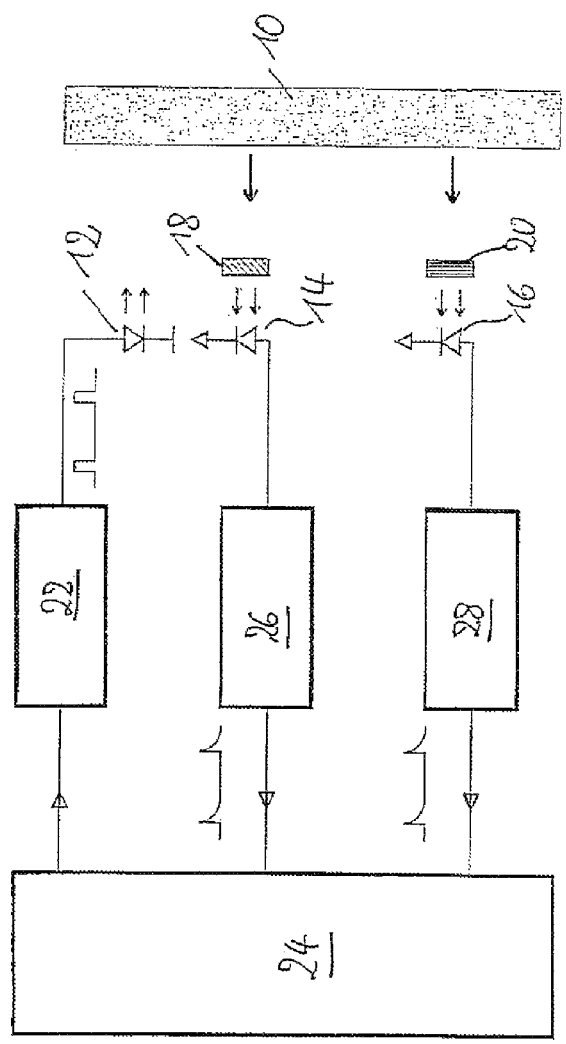
FIG. 1 shows a block diagram of a device according to an embodiment of the present teachings.

According to FIG. 1, an excitation light source 12 and two light-sensitive receivers 14 and 16 have been placed adjacent to a marking that contains one or more photoluminescent material(s) 10.

As used herein, the term "photoluminescent material" should be understood to encompass any material that is excitable to emit emission light by irradiating it with excitation light of one or more wavelengths. The excitation light may fall within the range from infrared to ultraviolet, inclusive of both infrared and ultraviolet. Depending on the composition and type of the photoluminescent material, the emission light can be higher in energy (shorter in wavelength) or lower in energy (longer in wavelength) than the excitation light. As is apparent from the foregoing, the excitation light (the excitation radiation) and/or the emission light (the emission radiation) can be outside the visible range.

The excitation light source 12 may be, e.g., an LED that radiates infrared light at 940 nm, or a laser diode that radiates infrared light at 980 nm. However, the type of light source is not particularly limited and a wide variety of light sources may be utilized, in addition or in the alternative, with the present teachings, such as incandescent, gas-discharge, chemo-luminescent, fluorescent, phosphorescent, etc. Also, the wavelength is not particularly limited, as was noted above and may generally fall anywhere within the range of $10^{-5}$ to $10^{-8}$ m (i.e. frequency range of $10^{12}$ to $10^{16}$ sec$^{-1}$).

The photosensitive receivers 14, 16 may comprise, e.g., photodiodes that are sensitive in an appropriate frequency range for the types of photoluminescent materials to be detected/identified. However, the present teachings are not particularly limited and a wide variety of photosensitive receiver may be utilized, in addition or in the alternative, with the present teachings, such as phototubes, photomultiplies, photo-resistors, charge-coupled devices, etc.

A filter 18, 20 may be disposed between each of the photosensitive receivers (sensors) 14 and 16, respectively, and the photoluminescent material 10. The filters 18, 20 preferably exhibit different spectral transparencies. The filters 18, 20 are preferably absorptive filters, but may also be interference or dichroic filters. For example, the filters 18, 20 may be plastic or glass based with appropriate pigments embedded therein to achieve the desired spectral transmission characteristics.

Figure 2:
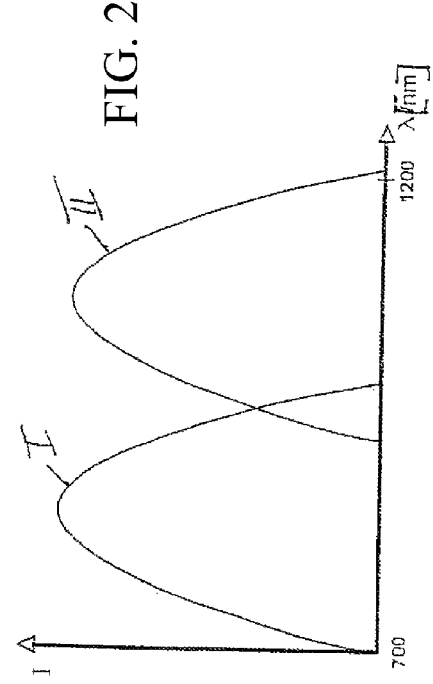
FIG. 2 shows transmission curves of representative filters used in the device of FIG. 1.

In FIG. 2, curve I shows the transparency D of the filter 18 over a range of wavelengths λ between about 700-1200 nm and it has a pronounced maximum at approximately 820 nm. Curve II shows the transparency of the filter 20 over the same range of wavelengths λ and it has a pronounced maximum at approximately 1080 nm. Thus, the filters 18, 20 can advantageously filter out wavelengths of the emission light that are outside of the sensitivity range of the respective photosensitive receivers, thereby improving the accuracy of the measurements, as will be further discussed below.

The excitation light source 12 is connected with a control and evaluation unit 24 via a transmitter unit 22. The transmitter unit 22 comprises an energy/power source, with which the excitation light source 12 is energizable at a predetermined time sequencing and at a predetermined power. That is, the transmitter unit 22 preferably contains known circuitry configured to convert control signals from the control and evaluation unit 24 into signals for driving the excitation light source 12 and may preferably comprise at least a power source and a FET that is (ultimately) driven by the control signals from the control and evaluation unit 24.

The photo-sensitive receivers 14 and 16 are each connected with the control and evaluation unit 24 via a receiver unit 26 and 28, respectively. The receiver units 26, 28 are constructed such that the output signals of the light-sensitive receivers 14, 16, respectively, are suppliable to the control and evaluation unit 24 in a temporally predetermined way. That is, the receiver units 26, 28 preferably each contains known circuitry configured to allow signals generated by the photosensitive receivers 14, 16 to pass through the receiver units to the control and evaluation unit 24 in a temporally predetermined way. The signals may be additionally processed in the receiver units, e.g. amplified.

The control and evaluation unit 24 preferably comprises known circuitry for processing such signals, including at least one microprocessor and program/data storage (memory), as well as input/output (I/O) devices and ports. The microprocessor(s) is (are) preferably programmed/configured to execute one or more of the functions described above and/or below.

Figure 3:
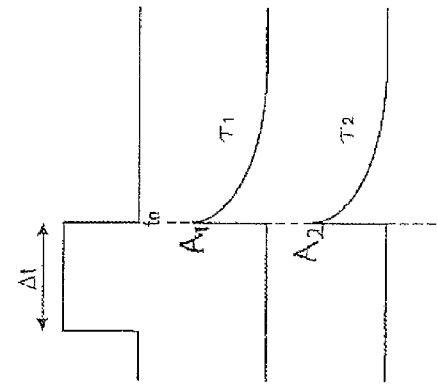
FIG. 3 shows time progressions of the intensities of the excitation light and the emission light of the photoluminescent material shown in FIG. 1.

According to the uppermost curve of FIG. 3, the transmitter unit 22 is controlled by the control and evaluation unit 24 such that the excitation light source 12 emits an excitation light pulse with a predetermined duration (Δt) and intensity. The excitation light pulse ends at time $t_0$.

The receiver units 26, 28 are activated at time $t_0$ and transmit signals from the photodiodes 14, 16 to the control and evaluation unit 24. These signals correspond to the emission light emitted from the photoluminescent material 10, as indicated by the downwardly sloping curves in FIG. 3.

The emission light decays approximately exponentially from a maximum intensity ($A_1$ and $A_2$) at time $t_0$. Due to the respective filters 18, 20, emission light components having different wavelengths and/or a different spectral composition irradiate the photodiodes 14, 16 and thus different signals are generated by the photodiodes 14, 16 and are respectively transmitted to the receiver units 26, 28.

More specifically, the two exponentially-decreasing emission light components shown in FIG. 3 can each be characterized by a maximum intensity $A_1$ and $A_2$, respectively, at time $t_0$ and a decay constant $\tau_1$ or $\tau_2$. An intensity function can be approximated and described generally for both of these emission lights according to the following equation (1):

$$y_i = Ae^{-(\tau \times i \times \Delta t)} + A_0. \tag{1}$$

Herein, the intensity $y_i$ is read out at a sampling interval $\Delta t$, wherein i indicates the number of samples that have been taken. A is the initial (maximum) intensity at time $t_0$, τ is the decay constant and $A_0$ is a constant ambient (background) light component. The value "i×Δt" represents the total time since the maximum intensity A of the material 10 was achieved at time $t_0$.

The control and evaluation unit 24 samples the temporal intensity curves transmitted from the receiver units 26 and 28, e.g., at a sampling rate of 10 μs. In such case, 250 samples require an evaluation time of 2.5 ms. The excitation light pulses may have a duration Δt, e.g., of approximately 500 μs and may be repeated, e.g., at intervals of 5 ms. Therefore, as indicated by the signals transmitted from the receiver units 26, 28 to the evaluation unit 24 in FIG. 1, a plurality of evaluations preferably may be performed in order to identify the material 10.

Function (1) as mentioned above is stored within the control and evaluation unit 24. By known mathematical methods or processes it is possible to determine the values of A and τ based upon the intensity curves of the emission light components transmitted from the receiver units 26 and 28 to the evaluation unit 24, i.e. $A_1$ and τ1 for the shorter-wavelength emission light component and A2 and τ2 for the longer-wavelength emission component.

To increase the accuracy of the calculation, for example, up to 256 (or more, if necessary) measurement cycles (each having 250 time-sequenced samples) may be performed and their samples may be averaged in a time-synchronous manner. In this case, A and τ can be calculated based upon on an averaged set of values according to equation (2):

$$(\hat{y}i|i \times \Delta t) = (1/n \times \Sigma yi|i\Delta t) \qquad (2)$$

The decay constants $\tau_1$ and $\tau_2$ are characteristic parameters of the photoluminescent material 10. These decay constants are independent of the initial (maximum) intensities $A_1$ and $A_2$, and can therefore be used directly for the identification or authentication of the photoluminescent material 10.

On the other hand, the initial intensities $A_1$ and $A_2$ can not be directly used for the identification or authentication of the photoluminescent material 10, because their respective magnitudes depend on the duration, intensity and wavelength(s) of the excitation light pulse, as well as on the concentration of the photoluminescent material 10.

Therefore, at least one intensity parameter, which is independent of the excitation light pulse and the concentration of the photoluminescent material 10, may be derived from the initial intensities $A_1$ and $A_2$ calculated by the control and evaluation unit 24. For example, the ratio of $A_1$ to $A_2$ may be determined. Or, the ratio x of the initial intensity $A_1$ to the total intensity $A_1+A_2$ and the ratio y of the initial intensity $A_2$ to the total intensity $A_1+A_2$ may be determined. Together with the decay constants, one or more these intensity parameters may be utilized to identify or authenticate the particular photoluminescent material 10.

With the arrangement according to FIG. 1, the intensity parameter(s) as well as the decay constants for predetermined (known) photoluminescent materials can be advantageously determined and stored prior to attempting to identify an unknown photoluminescent material. Then, when an unknown photoluminescent material is examined, it is only necessary to determine its characteristic values (e.g., at least one intensity parameter and at least two decay constants), which are then compared with the corresponding stored values. Therefore, an unknown photoluminescent material can be reliably identified by a positive comparison with the stored values.

Figure 4:
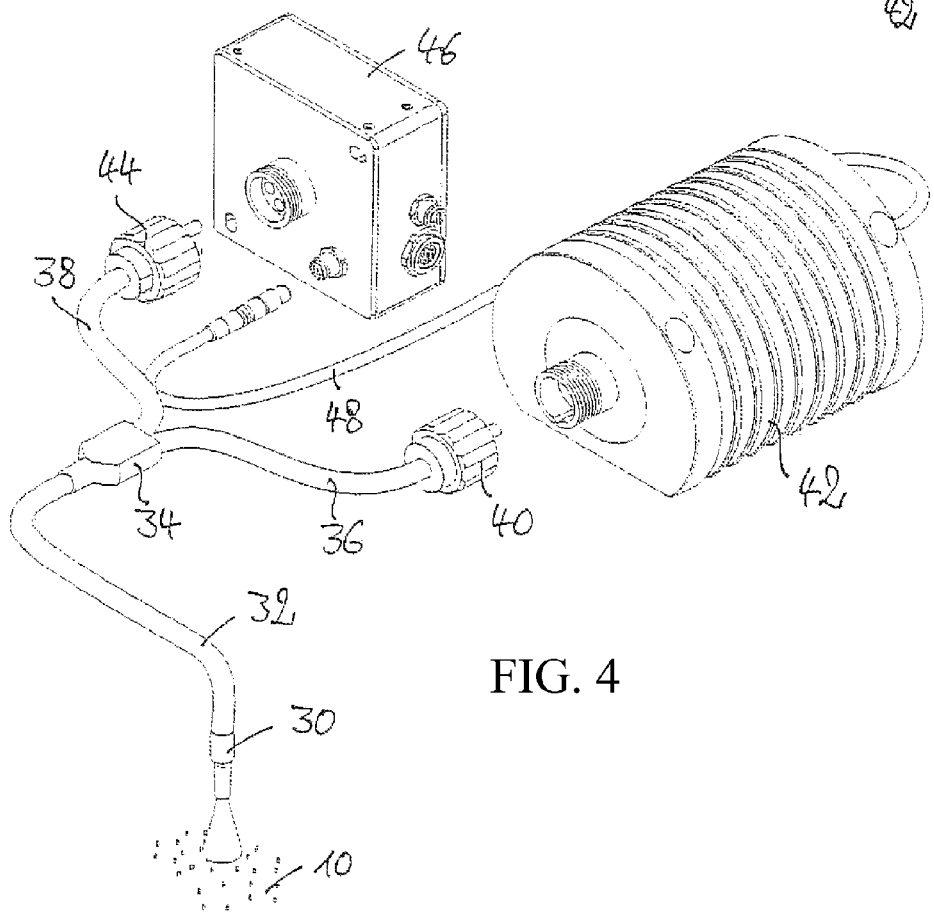
FIG. 4 shows a schematic perspective view of a further development of the device of FIG. 1.

FIG. 4 shows a perspective view of an exemplary further development of the device according to FIG. 1.

An optical fiber bundle 32 leads from a sensor head 30 to a divider 34 that separates the bundle 32 into a transmitter light guide 36 and a receiver light guide 38.

The transmitter light guide 36 is connected via an adapter 40 to a transmitter 42, which comprises the above-described transmitter unit 22 and excitation light source 12. Therefore, the excitation light generated by the light source 12 is transmitted to the sensor head 30 via one or more optical fiber(s) in the transmitter light guide 36, in order to irradiate the photoluminescent material 10.

Two or more of the optical fibers in the receiver light guide 38 may be divided at an adapter 44 for analysis of two or more different emission light components, which are emitted by the photoluminescent material 10 in response to being irradiated by the excitation light. The adapter 44 is coupled to a housing 46 that contains the above-described control and evaluation unit 24, receiver units 26, 28, and filters 18, 20 respectively associated with the individual emission light components. The filters 18, 20 can be disposed directly in respective female connectors 47 provided in the housing 46. That is, each optical fiber or bundle of optical fibers within the receiver light guide 38 provided for a single emission light component is inserted into a separate female connector 47 that is coupled to one of the receiver units 26, 28.

In the embodiment of FIG. 1, a division of the excitation light into two emission light components was described. However, in the embodiment of FIG. 4, three emission light components may be analyzed as indicated by the three female connectors 47 shown in FIG. 5, which is a front view of the housing 46 shown in FIG. 4.

The transmitter 42 is connected with the housing 46 via a control line 48 in order to enable the control and evaluation unit 24 to control the operation of the transmitter 42, in particular to control the duration and power of the excitation light emitted from the excitation light source 12 via the optical fiber guide 32 to irradiate the photoluminescent material 10.

Figure 6:
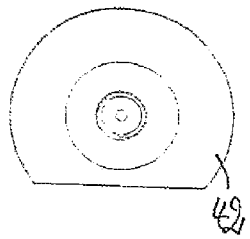
FIG. 6 shows a rear view of the transmitter shown in FIG. 4.

FIG. 6 shows a rear view of the transmitter 42 with the input coupling (not numbered) for the control line 48.

Figure 7:
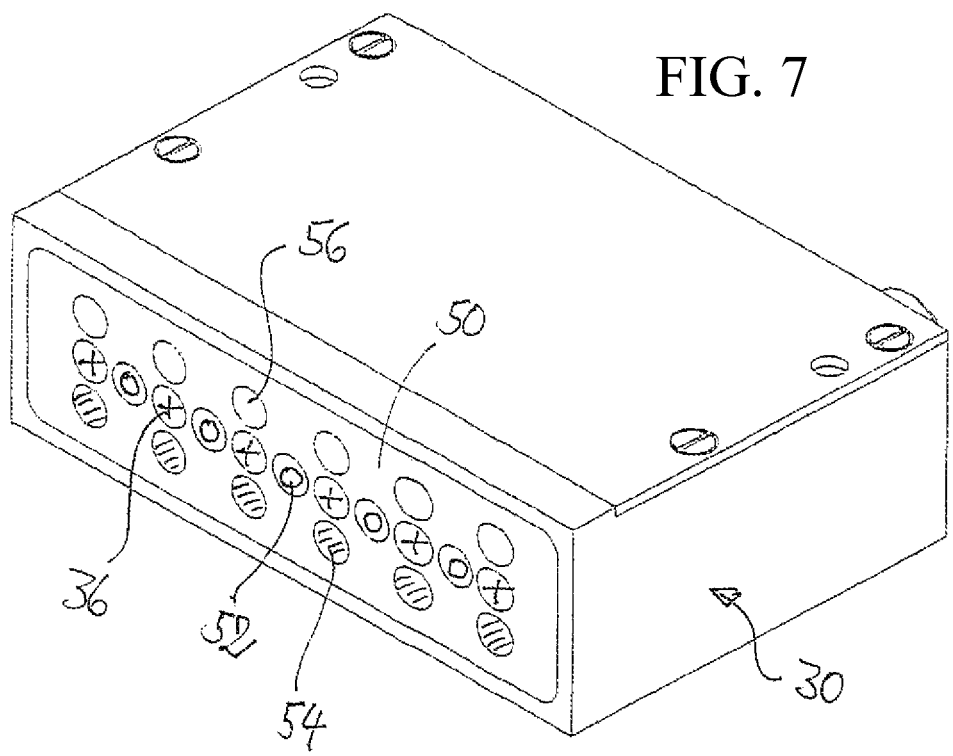
FIG. 7 shows a representative sensor (window) surface of a further development of the device of FIGS. 1 and 4.

FIG. 7 shows an exemplary embodiment of a sensor surface 50 of a sensor head 30 according to a further development of the present teachings.

Exit surfaces of transmitter light guides 36 (indicated by crosses) and entry surfaces of three groups of receiver light guides 52 (indicated by circles), 54 (indicated by hatching) and 56 (empty) are defined in or on the sensor surface 50. Each group of the receiver light guides 52, 54 and 56 guides emission light emitted from the photoluminescent material 10 to one of associated filters and then to the associated receiver unit, which are accommodated in the housing 46 of FIG. 4.

As is apparent from FIG. 7, the end surfaces of the light guides are disposed such that photoluminescent material 10 facing the sensor surface 50 (FIG. 4) is illuminated/irradiated with excitation light over a relatively large surface area and the emitted emission light is received by the sensor surface 50 over a relatively large area.

Figure 5:
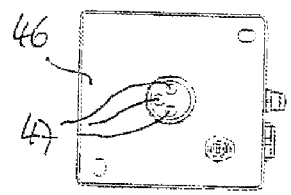
FIG. 5 shows a front view of the housing shown FIG. 4.

A first embodiment of a device according to the present teachings was described with reference to FIGS. 1 to 3, in which two emission light components having a frequency or wavelength range set by the transmission curves of the filters 18 and 20 are detected. In FIGS. 4 and 5, exemplary examples were described in which at least three filters are provided and accordingly at least three emission light components are detected and evaluated.

In general, the above-described function (1) for evaluating and determining the intensity parameter using decay constants can be more accurately optimized when each detected emission light component is dominated more substantially or completely by one wavelength. Depending on the passband of the filter and the emission spectrum of the photoluminescent material 10, it can be expedient to use the following function (3) instead of function (1):

$$y_i = \sum_{j=0}^{m} A_j e^{-(\tau_j \times i \times \Delta t)} + A_0, \qquad (3)$$

wherein:

$y_i$=the intensity of an emission light component at time $i \times \Delta t$, wherein i is the number of samples and $\Delta t$ is the sampling interval (the inverse of the sampling rate), $A_j$=the initial (maximum) intensity of one part (e.g., one wavelength or a range of wavelengths) of the emission light component, $\tau_j$=the decay parameter of the one (same) part (e.g., one wavelength or a range of wavelengths) of the emission light component, j=the number of parts (e.g., one wavelength or a range of wavelengths) in the emission light component and $A_0$=a constant ambient (background) light component.

The above formula takes into account that the emission light contained in an emission light component has a number of different (separate) spectral portions (j) that add up to the total intensity of the emission light component. At the minimization of the deviation between the measured total intensity of the emission light components and the intensity of the emission light components given by formula (3), a plurality of parameters $A_j$ and $\tau_j$ are calculated, wherein the decay parameters $\tau_j$ are directly identified for the respective photoluminescent material and the initial intensities $A_j$ are normalized, in that they are each set in relation to the sum of the initial intensities of all portions of an emission light component.

REFERENCE NUMBER LIST 10 photoluminescent material
12 excitation light source
14 light-sensitive receiver
16 light-sensitive receiver
18 filter
20 filter
22 transmitter unit
24 control and evaluation unit
26 receiver unit
28 receiver unit
30 sensor head
32 light guide bundle
34 divider
36 transmitter light guide
38 receiver light guide
40 adapter
42 transmitter
44 adapter
46 housing
48 control line
50 sensor surface
52 receiver light guide

The invention claimed is:

1. A method for identifying a photoluminescent material that, after excitation with excitation light, emits emission light having different wavelengths, the method comprising:
    irradiating the photoluminescent material with the excitation light so that the photoluminescent material emits at least first and second emission light components having different wavelengths, respectively, as a result of the excitation,
    after turning off the excitation light, detecting temporal intensity curves of the at least first and second emission light components,
    calculating respective initial intensities of the at least first and second emission light components at a common time,
    determining at least one intensity parameter by correlating the at least two calculated initial intensities,
    determining at least one decay parameter value for each emission light component from the detected temporal intensity curves of the at least first and second emission light components and
    identifying the photoluminescent material based upon the at least one intensity parameter and the at least two decay parameter values.

2. The method according to claim 1, wherein the photoluminescent material is excited with an excitation light pulse of a predetermined wavelength and the initial intensities of the first and second emission light components are calculated for a time point that is immediately after termination of the excitation light pulse.

3. The method according to claim 2, wherein the photoluminescent material is an up-converting material and the wavelength(s) of the excitation light is/are longer than the wavelengths of the detected emission light components.

4. The method according to claim 3, wherein the step of identifying the photoluminescent material comprises:
    optimally fitting a first predetermined intensity function of the first emission light component, which includes at least one initial intensity parameter and one decay parameter value, to the detected temporal intensity curve of the first emission light component, and
    optimally fitting a second predetermined intensity function of the second emission light component, which includes at least one initial intensity parameter and one decay parameter value, to the detected temporal intensity curve of the second emission light component.

5. The method according to claim 4, wherein the first and second predetermined intensity functions are determined according to the equation:

$$y_i = \sum_{j=0}^{m} A_j e^{-(\tau j \times i \times \Delta t)} + A_0,$$

wherein:
    $y_i$=the intensity of an emission light component at time $i \times \Delta t$, wherein i is the number of samples and $\Delta t$ is the sampling interval,
    $A_j$=the initial intensity of one part of the emission light component,
    $\tau_j$=the decay parameter value of the one part of the emission light component,
    j=the number of parts in the emission light component and
    $A_0$=a constant ambient light component.

6. The method according to claim 5, wherein the first and second predetermined intensity functions are determined according to the equation:

$$y_i = A e^{-(\tau \times i \times \Delta t)} + A_0,$$

wherein:
    $y_i$=the intensity of one emission light component at time $i \times \Delta t$, wherein i is the number of samples and $\Delta t$ is the sampling interval,
    A=the initial intensity of the one emission component,
    $\tau$=the decay parameter value of the one emission light component, and
    $A_0$=a constant ambient light component.

7. The method according to claim 6, wherein the step of identifying the photoluminescent material further comprises:
    comparing the at least one determined intensity parameter and the at least two determined decay parameters with a plurality of stored values of predetermined intensity parameters and predetermined decay parameter values for a plurality of known photoluminescent materials.

8. The method according to claim 1, wherein the photoluminescent material is an up-converting material and the wavelength(s) of the excitation light is/are longer than the wavelengths of the detected emission light components.

9. The method according to claim 1, wherein the step of identifying the photoluminescent material comprises:
    optimally fitting a first predetermined intensity function of the first emission light component, which includes at least one initial intensity parameter and one decay parameter value, to the detected temporal intensity curve of the first emission light component, and optimally fitting a second predetermined intensity function of the second emission light component, which includes at least one initial intensity parameter and one decay parameter value, to the detected temporal intensity curve of the second emission light component.

10. The method according to claim 9, wherein the first and second predetermined intensity functions are determined according to the equation:

$$y_i = \sum_{j=0}^{m} A_j e^{-(\tau j \times i \times \Delta t)} + A_0,$$

wherein:
$y_i$=the intensity of an emission light component at time $i \times \Delta t$, wherein i is the number of samples and $\Delta t$ is the sampling interval,
$A_j$=the initial intensity of one part of the emission light component,
$\tau_j$=the decay parameter value of the one part of the emission light component,
j=the number of parts in the emission light component and
$A_0$=a constant ambient light component.

11. The method according to claim 9, wherein the first and second predetermined intensity functions are determined according to the equation:

$$y_i = Ae^{-(\tau \times i \times \Delta t)} + A_0,$$

wherein:
$y_i$=the intensity of one emission light component at time $i \times \Delta t$, wherein i is the number of samples and $\Delta t$ is the sampling interval,
A=the initial intensity of the one emission component,
$\tau$=the decay parameter value of the one emission light component, and
$A_0$=a constant ambient light component.

12. The method according to claim 9, wherein the step of identifying the photoluminescent material further comprises:
comparing the at least one determined intensity parameter and the at least two determined decay parameter values with a plurality of stored values of predetermined intensity parameters and predetermined decay parameter values for a plurality of known photoluminescent materials.

13. A device configured to identify a photoluminescent material that, after being excited with excitation light, emits emission light comprising at least two different wavelengths, the device comprising:

an excitation light source configured to irradiate the photoluminescent material,
a receiving apparatus configured to detect the emission light emitted from the photoluminescent material due its excitation with the excitation light, the receiving apparatus including at least two receiver units configured to respectively detect emission light components having different wavelengths,
an evaluation apparatus configured to evaluate the emission light components detected by the receiver units with regard to their intensities and their time progression and
a controller configured to control operation of the excitation light source and the evaluation apparatus in accordance with the method of claim 1.

14. The device according to claim 13, further comprising:
a storage apparatus that stores values of intensity parameters and decay parameter values of a plurality of known photoluminescent materials and
a comparison apparatus configured to compare determined intensity parameters and determined decay parameter values with the corresponding stored values.

15. The device according to claim 14, wherein the receiver units respectively comprise optical filters having different wavelength-dependent transparencies.

16. The device according to claim 15, further comprising:
a light guide optically coupled with the excitation light source and the receiver units, and
a sensor head optically coupled to an opposite end of the light guide.

17. The device according to claim 16, wherein end surfaces of the light guide optically coupled with the excitation light source and the receiver units are respectively disposed in a distributed manner over a wide portion of a sensor surface of the sensor head.

18. The device according to claim 13, wherein the receiver units respectively comprise optical filters having different wavelength-dependent transparencies.

19. The device according to claim 13, further comprising:
a light guide optically coupled with the excitation light source and the receiver units, and
a sensor head optically coupled to an opposite end of the light guide.

20. The device according to claim 19, wherein end surfaces of the light guide optically coupled with the excitation light source and the receiver units are respectively disposed in a distributed manner over a wide portion of a sensor surface of the sensor head.

* * * * *